United States Patent [19]

Seki et al.

[11] Patent Number: 4,501,606

[45] Date of Patent: Feb. 26, 1985

[54] HERBICIDAL 5-T-BUTYL-3-PYRAZALYLCARBAMATES AND UREAS

[75] Inventors: Nansho Seki; Yuki Yamaguchi; Yukihiro Nakamura; Hiroshi Kubo; Tetsuo Tsuruya, all of Tokyo, Japan

[73] Assignee: Showa Denko Kabushiki Kaisha, Tokyo, Japan

[21] Appl. No.: 467,630

[22] Filed: Feb. 18, 1983

[30] Foreign Application Priority Data

Feb. 18, 1982 [JP] Japan .................................. 57-23668
Feb. 18, 1982 [JP] Japan .................................. 57-23669
Nov. 8, 1982 [JP] Japan .................................. 57-194592

[51] Int. Cl.³ .................... A01N 43/56; C07D 231/38
[52] U.S. Cl. ......................................... 71/92; 548/362
[58] Field of Search ............................ 548/362; 71/92

[56] References Cited

U.S. PATENT DOCUMENTS 3,754,887  8/1973  Brantley ................................. 71/92

FOREIGN PATENT DOCUMENTS 1598900  9/1981  United Kingdom .

OTHER PUBLICATIONS

Vogel et al., Chem. Abst., 83, 43280x (1975).

Primary Examiner—Henry R. Jiles
Assistant Examiner—Kurt G. Briscoe
Attorney, Agent, or Firm—Sughrue, Mion, Zinn, Macpeak & Seas

[57] ABSTRACT

A novel pyrazole derivative represented by the formula [I]:

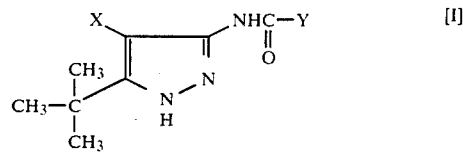

wherein X and Y are defined in the specification, which has herbicidal activity, is disclosed. A process for preparing the pyrazole derivative of the formula [I] is also disclosed. A herbicide containing as an active ingredient the pyrazole derivative of the formula [I] is further disclosed as is a method for using the herbicide.

9 Claims, No Drawings

HERBICIDAL 5-T-BUTYL-3-PYRAZALYLCARBAMATES AND UREAS

FIELD OF THE INVENTION

The present invention relates to novel pyrazole derivatives compounds and more particularly to 5-butyl-3-pyrazolylcarbamates and ureas, and their method of preparation and use as herbicides.

SUMMARY OF THE INVENTION

This invention is comprised of novel pyrazole derivatives, in particular, 5-t-butyl-3-pyrazolylcarbamates and ureas represented by the formula [I]:

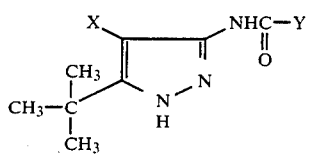

wherein X is a hydrogen atom, a chlorine atom, or a bromine atom; and Y is (1) an —OR group wherein R is a lower alkyl group, a lower alkenyl group, or a lower alkynyl group, or (2) an

group wherein R' and R" which may be the same or different, are each a lower alkyl group. In the above, the lower alkyl group, lower alkenyl group, and lower alkynyl group are each preferably those having 1 to 4 carbon atoms. This invention is also comprised of a process for preparing compounds of the formula [I]. This invention is further comprised of a herbicide containing compounds of the formula [I] as an active ingredient and a method of using the herbicide.

DETAILED DESCRIPTION OF THE PREFERRED EMBODIMENTS

With respect to the compound of the formula [I], there is a possible tautomer represented by the formula [I'] as illustrated below.

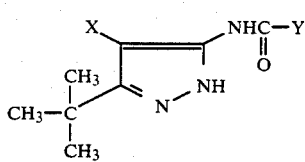

However, in the following explanation, this tautomer is representatively expressed by the formula [I].

The compound of the formula [I] is characterized by having a t-butyl group at the 5-position of the pyrazole ring thereof, such characteristic together with the other characteristics having a great meaning in herbicidal activity.

The compound of the formula [I] exhibits strong herbicidal activity against a wide range of weeds, and if it is applied to the weeds in the amount of from 0.5 to 10 kg/ha before the emergence of the weeds or at the early growth stage thereof, it can control a wide range of the weeds.

In other words, when the application amount of the compound of this invention is controlled, or an appropriate application method is employed, it can selectively control various weeds which grow in cultivation fields for crops, such as corn, potato, sugar beet, peanuts, soybeans, sunflower, barley, wheat, sorghum, cotton, fruits and the like.

Typical compounds according to this invention are shown in Table 1 below. Among these, particularly preferred compounds are methyl N-(5-t-butyl-3-pyrazolyl)carbamate, allyl N-(5-t-butyl-3-pyrazolyl)carbamate, propargyl N-(5-t-butyl-3-pyrazolyl)carbamate and N,N-dimethyl-N'-(5-t-butyl-3-pyrazolyl)urea.

TABLE 1

| Compound No. | X | Y | Melting Point (°C.) | NMR Analysis Data* H—NMR [δ value (ppm)] |
|---|---|---|---|---|
| 1 | H | —OCH$_3$ | 177 | 1.30 (s, 9H), 3.78 (s, 3H), 6.25 (s, 1H), 8.7 (br, 1H), 10–12 (br, 1H) |
| 2 | H | —OC$_2$H$_5$ | 157 | 1.30 (tr, 3H, J = 7), 1.30 (s, 9H), 4.24 (q, 2H, J = 7), 6.30 (s, 1H), 8.7 (br, 1H), 9.5–10.0 (br, 1H) |
| 3 | H | —OC$_3$H$_7$—iso | 134–136 | 1.30 (d, 6H, J = 7), 1.30 (s, 9H), 4.5–5.5 (m, 1H), 6.30 (s, 1H), 8–9 (br, 1H), 9–11 (br, 1H) |
| 4 | H | —OC$_4$H$_9$—n |  | 0.94 (tr, 3H, J = 7), 1.30 (s, 9H), 1–2 (m, 4H), 4.2 (tr, 2H, J = 7), 6.32 (s, 1H), 8–9 (br, 1H), 9.5–10.5 (br, 1H) |
| 5 | H | —OC$_4$H$_9$—iso | 140–142 | 0.96 (d, 6H, J = 7), 1.30 (s, 9H), 1.5–2.5 (m, 1H), 3.98 (d, 2H, J = 7), 6.32 (s, 1H), 8.5–9 (br, 1H), 9.5–10.5 (br, 1H) |
| 6 | Cl | —OCH$_3$ |  | 1.39 (s, 9H), 3.81 (s, 3H), 7–8 (br, 1H) |
| 7 | Br | —OCH$_3$ | 148–149 | 1.39 (s, 9H), 3.78 (s, 3H), 7.45 (br, 1H), 10–11 (br, 1H) |
| 8 | H | —OCH$_2$CH=CH$_2$ | 131–132 | 1.30 (s, 9H), 4.68 (d, 2H), 5.0–5.5 (m, 2H), 5.5–6.0 (m, 1H), (6.32 (s, 1H), 8.8 (br, 1H) |
| 9 | H | —OCH$_2$C=CH$_2$ \| CH$_3$ | 120–121 | 1.30 (s, 9H), 1.79 (s, 3H), 4.61 (s, 2H), 4.9–5.1 (br, 2H), 6.33 (s, 1H), 9.0 (br, 1H) |
| 10 | H | —OCH$_2$C≡CH | 187–188 | 1.30 (s, 9H), 2.50 (tr, 1H), 4.78 (d, 2H), |

TABLE 1-continued

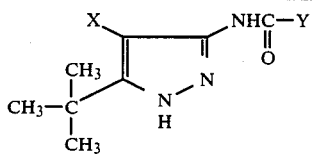

| Compound No. | X | Y | Melting Point (°C.) | NMR Analysis Data* H—NMR [δ value (ppm)] |
|---|---|---|---|---|
| | | | | 6.33 (s, 1H), 9.0 (br, 1H) |
| 11 | Cl | —OCH₂C≡CH | 132–133 | 1.39 (s, 9H), 2.52 (tr, 1H, 4.80 (d, 2H) |
| 12 | Br | —OCH₂C≡CH | | 1.40 (s, 9H), 2.52 (tr, 1H), 4.81 (d, 2H) |
| 13 | H | —N(CH₃)CH₃ | 220–222 | 1.22 (s, 9H), 2.87 (s, 6H), 6.03 (s, 1H), 8.5 (br, 1H), 11.7 (br, 1H) |
| 14 | Cl | —N(CH₃)CH₃ | 178–180 | 1.37 (s, 9H), 3.00 (s, 6H), 7–8 (br, 1H) |
| 15 | Br | —N(CH₃)CH₃ | 123–124 | 1.43 (s, 9H), 3.10 (s, 6H), 6.5–8 (br, 1H) |
| 16 | H | —N(C₂H₅)C₂H₅ | 218–220 | 1.08 (tr, 6H, J = 7), 1.25 (s, 9H), 3.32 (q, 4H, J = 7), 6.05 (s, 1H), 8.3 (br, 1H) |

*The NMR analysis was carried out in CDCl₃ at 60 MHz in which tetramethylsilane was used as an internal standard, and symbols of s, d, tr, q, m, br, and J stand for singlet, doublet, triplet, quartet, multiplet, broad peak, and coupling constant.
In the measurement of Compound Nos. 1, 7, 9, 13 and 14, a slight amount of DMSO was added.

The compound of the formula [I] can be prepared as follows:

Method (A)

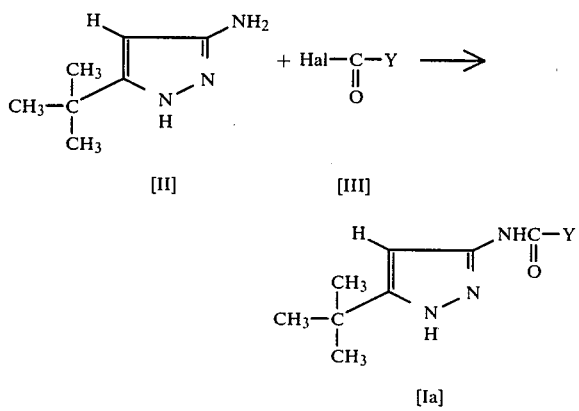

In the above reaction scheme, Y is the same as defined above, and Hal is a halogen atom, e.g., a chlorine atom or a bromine atom.

The compound of the formula [Ia] can be prepared from 3-amino-5-t-butylpyrazole [II] and a haloformate or carbamoyl halide [III].

This reaction is carried out by adding dropwise the haloformate or carbamoyl halide to the aminopyrazole dissolved in a solvent. Any solvent which is stable under the reaction condition and does not react with or decompose the starting materials and desired compound can be used in this invention. Suitable examples of the solvent which can be used include aliphatic hydrocarbons (e.g., hexane, heptane, petroleum ether, cyclohexane, etc.), aromatic hydrocarbons (e.g., benzene, toluene, xylene, ethylbenzene, cumene, etc.), halogenated hydrocarbons (e.g., carbon tetrachloride, chloroform, dichloromethane, ethylene chloride, dichloropropane, trichloroethylene, tetrachloroethylene, chlorobenzene, etc.), ethers (e.g., diethyl ether, tetrahydrofuran, dioxane, etc.), ketones (e.g., acetone, methyl ethyl ketone, methyl isobutyl ketone, cyclohexanone, etc.), esters (e.g., ethyl acetate, etc.), nitriles (e.g., acetonitrile, etc.) and the like. These solvents can be used alone or in admixture.

Where [III] is a haloformate, this reaction should be carried out without a base to avoid the reaction at the N-atom of the pyrazole ring. But where [III] is a carbamoyl halide, it is in general desired to use an organic or inorganic base as a promoter in order to carry out the reaction under a mild condition. Suitable examples of the organic base which can be used include aliphatic or aromatic tertiary amines (e.g., triethylamine, pyridine, picoline, quinoline, etc.) and the like, and suitable examples of the inorganic base which can be used include alkali metal carbonates (e.g., sodium carbonate, potassium carbonate, etc.), alkali metal bicarbonates (e.g., sodium bicarbonate, potassium bicarbonate, etc.), alkali metal hydroxides (e.g., sodium hydroxide, potassium hydroxide, etc.), alkaline earth metal carbonates (e.g., calcium carbonate, etc.), alkaline earth metal hydroxides (e.g., calcium hydroxide, etc.) and the like.

Also, this reaction may be carried out by using water as the solvent. In this case, the pH of the solution should be maintained around neutral. For example, a haloformate is added dropwise to the aqueous solution of the starting aminopyrazole and a weak inorganic base. The mixture is allowed to react, and a solid product is collected by filtration. Suitable examples of the weak inorganic base which can be used include sodium bicarbonate, potassium bicarbonate and so on.

A molar proportion of the haloformate or carbamoyl halide to the aminopyrazole of the formula [II] is not restricted but in general can be used suitably in a range of from 1.0:1 to 1.2:1. In this case, when the amount of the latter is too large, then unreacted products remain, whereas when the amount of the former is too large, then the NH moiety on the pyrazole ring more likely reacts.

When the promoter is used, a suitable molar proportion thereof to the aminopyrazole of the formula [II] is in a range of from 1.0:1 to 2.0:1, preferably 1.0:1 to 1.2:1.

The reaction can be carried out at a temperature ranging from 0° C. to 150° C., preferably from 40° C. to 120° C., but when water is used as the solvent, it is preferred to employ a low temperature of around 0° C.

A suitable time of the reaction is in a range of from 0.5 to 10 hours, preferably 1 to 5 hours.

The method of isolation of the desired product varies with the kinds of starting materials and solvent. For example, it can be isolated by a method in which after completion of the reaction, water or a diluted alkaline solution is added to the reaction mixture to form crystals which are then filtered and washed with water for recovery, or a method in which after completion of the reaction, water or a diluted alkaline solution is added to the reaction mixture, the mixture is shaken, and the organic layer is concentrated and subjected to crystallization from a solvent such as hexane, etc. or a method in which after completion of the reaction, the solvent is distilled off, and a diluted alkaline solution and a solvent such as hexane are added to the residue to form crystals.

Method (B)

The compound of the formula [Ia] can be easily subjected to chlorination or bromination at the 4-position thereof by the use of respective reagents in a conventional method.

The chlorination can be carried out by reacting the compound of the formula [Ia] dissolved or suspended in a solvent with a chlorinating agent such as chlorine, sulfuryl chloride, etc. Examples of the solvent which can be used are those which do not react with the chlorinating agent, such as halogenated hydrocarbons, e.g., dichloromethane, carbon tetrachloride, chloroform, ethylene dichloride, dichloropropane, etc. The reaction temperature is suitably in a range of from 0° C. to 70° C., preferably from 10° C. to 40° C. A suitable molar ratio of the chlorinating agent to the compound of the formula [Ia] is in a range of from 1.0:1 to 1.5:1, preferably from 1.0:1 to 1.3:1. The reaction time is suitably in a range of from 1 to 3 hours.

The chlorination can further be carried out in the following manner. In other words, the compound of the formula [Ia] is dissolved in hydrochloric acid, and a chloric acid salt such as sodium chlorate, potassium chlorate, etc. is added dropwise thereto, followed by allowing the mixture to react. After completion of the reaction, the reaction product is neutralized with an aqueous alkaline solution whereby the desired product is crystallized.

The bromination can be carried out by reacting the compound dissolved or suspended in a solvent with a brominating agent such as bromine, etc. Examples of the solvent which can be used are those which do not react with the brominating agent, such as chlorinated hydrocarbons, e.g., dichloromethane, carbon tetrachloride, chloroform, ethylene dichloride, dichloropropane, etc., acetic acid and the like. The reaction temperature is suitably in a range of from 0° C. to 60° C., preferably from 0° C. to 30° C., and a suitable molar ratio of the brominating agent to the compound of the formula [Ia] is in a range of from 1.0:1 to 1.2:1.

The compound of the formula [I] which can be prepared by the respective reactions described above is, in general, sparingly soluble in water as well as benzene, toluene, carbon tetrachloride, hexane, etc., but it is easily soluble in alcohols, dimethylformamide and dimethyl sulfoxide and acetone.

The aminopyrazole of the formula [II] which can be used as the starting material can bre prepared by reacting cyanopinacoline and hydrazine in a solvent as illustrated in the following reaction scheme.

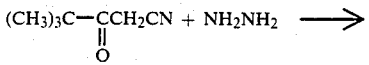

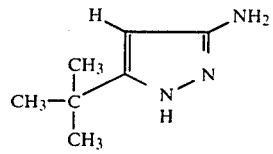

[II]

Examples of the solvent which can be used are those which do not react with the starting materials and desired product, such as alcohols, e.g., methanol, ethanol, etc. and the like. The reaction temperature is suitably in a range of from 30° C. to 100° C., and a suitable molar ratio of hydrazine to cyanopinacoline is in a range of from 1.0:1 to 1.5:1. In the above reaction, cyanopinacoline which can be used as the starting material can be prepared by a method described by, for example, Ber., 44 2065 (1911) or Japanese Patent Application (OPI) No. 137908/78.

The present invention is described in greater detail with reference to the following examples.

REFERENCE EXAMPLE

Preparation of 3-Amino-5-t-butylpyrazole [II]

125 g (1 mole) of cyanopinacoline was dissolved in 200 ml of ethanol, and 55 g of hydrazine hydrate was added thereto, followed by heating the mixture under reflux conditions for 2 hours. After completion of the reaction, the ethanol was distilled off, and an alkaline solution was added to the residue. The mixture was extracted with 500 ml of benzene, and the benzene layer was dried over anhydrous sodium sulfate, followed by distilling off the benzene. The resulting residue was allowed to stand for solidification whereby 131 g of 3-amino-5-t-butylpyrazole was obtained.

EXAMPLE 1

Preparation of Methyl N-(5-t-Butyl-3-pyrazolyl)carbamate (Compound No. 1)

10 g of 3-amino-5-t-butylpyrazole as prepared in Reference Example (this pyrazole compound being hereinafter referred to as "Compound [II]") was dissolved in 100 ml of carbon tetrachloride, and 6.8 g of methyl chloroformate was added to the solution. The mixture was then allowed to react for 5 hours under refluxing. After cooling the reaction solution, a potassium carbonate aqueous solution was added thereto whereby crystals were formed. The crystals were collected by filtration, and washed with carbon tetrachloride and water to obtain 3.8 g of methyl N-(5-t-butyl-3-pyrazolyl)carbamate. This compound was recrystallized from a mixed solvent of carbon tetrachloride and chloroform and found to have a melting point of 177° C.

EXAMPLE 2

Preparation of Ethyl N-(5-t-Butyl-3-pyrazolyl)carbamate (Compound No. 2)

2.8 g of Compound [II] was dissolved in 30 ml of dioxane, and 2.2 g of ethyl chloroformate was added to the solution. The mixture was then allowed to react for 5 hours under refluxing. After completion of the reaction, the solvent was distilled off, and hexane and a potassium carbonate aqueous solution were added to the residue to form crystals. The crystals were collected by filtration and washed with water and hexane to obtain 1.1 g of ethyl N-(5-t-butyl-3-pyrazolyl)carbamate.

EXAMPLE 3

The same procedures as used in Example 2 were repeated except using isopropyl chloroformate, n-butyl chloroformate and isobutyl chloroformate, respectively in place of the ethyl chloroformate. Thus, isopropyl N-(5-t-butyl-3-pyrazolyl)carbamate (Compound No. 3), n-butyl N-(5-t-butyl-3-pyrazolyl)carbamate (Compound No. 4), and isobutyl N-(5-t-butyl-3-pyrazolyl)carbamate (Compound No. 5) were obtained.

EXAMPLE 4

Preparation of Methyl N-(5-t-Butyl-4-chloro-3-pyrazolyl)carbamate (Compound No. 6)

2 g of Compound No. 1 as prepared in Example 1 was suspended in 30 ml of carbon tetrachloride, and 1.4 g of sulfuryl chloride was added dropwise to the suspension with stirring at 20° C. to 25° C. The mixture was allowed to react for an additional 2 hours, and a sodium carbonate aqueous solution was then added to the reaction solution. The organic layer was collected, and the solvent was distilled off. The residue was crystallized by the addition of hexane to obtain 1.0 g of methyl N-(5-t-butyl-4-chloro-3-pyrazolyl)carbamate.

EXAMPLE 5

Preparation of Methyl N-(5-t-Butyl-4-bromo-3-pyrazolyl)carbamate (Compound No. 7)

2 g of Compound No. 1 as prepared in Example 1 was dissolved in 30 ml of acetic acid, and 1.6 g of bromine was added to the solution. The mixture was allowed to react at room temperature for 2 hours. After completion of the reaction, the reaction solution was poured into ice water to thereby bring about crystallization. Thus, 1.5 g of methyl N-(5-t-butyl-4-bromo-3-pyrazolyl)carbamate was obtained.

EXAMPLE 6

Preparation of Allyl N-(5-t-Butyl-3-pyrazolyl)carbamate (Compound No. 8)

5.5 g of Compound [II] was dissolved in 30 ml of dioxane, and 4.2 g of allyl chloroformate was added to the solution. The mixture was allowed to react for 8 hours under refluxing. After completion of the reaction, the solvent was distilled off, and hexane and a potassium carbonate aqueous solution were added to the residue to form crystals. Thus, 3.4 g of allyl N-(5-t-butyl-3-pyrazolyl)carbamate was obtained. This compound was recrystallized from hydrous methanol and found to have a melting point of 131° C. to 132° C.

EXAMPLE 7

The same procedures as used in Example 6 were repeated except using 2-methylallyl chloroformate and propargyl chloroformate, respectively in place of allyl chloroformate. Thus, 2-methylallyl N-(5-t-butyl-3-pyrazolyl)carbamate (Compound No. 9) and propargyl N-(5-t-butyl-3-pyrazolyl)carbamate (Compound No. 10) were obtained.

EXAMPLE 8

Preparation of Propargyl N-(5-t-Butyl-4-chloro-5-pyrazolyl)carbamate (Compound No. 11)

1.5 g of Compound No. 10 as prepared in Example 7 was suspended in 30 ml of carbon tetrachloride, and 1 g of sulfuryl chloride was added thereto with stirring at room temperature. The mixture was allowed to react with stirring for 2 hours. After completion of the reaction, a potassium carbonate aqueous solution was added to the reaction solution and stirred. Thereafter, the carbon tetrachloride layer was separated off, and the layer was washed with water and dried over anhydrous sodium sulfate. The resultant was concentrated and subjected to crystallization by the addition of hexane. Thus, 1.2 g of propargyl N-(5-t-butyl-4-chloro-3-pyrazolyl)carbamate was obtained.

EXAMPLE 9

Preparation of Propargyl N-(5-t-Butyl-4-bromo-3-pyrazolyl)carbamate (Compound No. 12)

1.5 g of Compound No. 10 as prepared in Example 7 was dissolved in 20 ml of acetic acid, and 1.1 g of bromine was added to the solution. The mixture was allowed to react at room temperature for 2 hours. The reaction solution was poured into ice water and neutralized with a sodium hydroxide aqueous solution while stirring. The solids were separated to obtain 1.2 g of propargyl N-(5-t-butyl-4-bromo-3-pyrazolyl)carbamate.

EXAMPLE 10

Preparation of N,N-Dimethyl N'-(5-t-Butyl-3-pyrazolyl)urea (Compound No. 13)

4.2 g of Compound [II] and 3.2 g of triethylamine were dissolved in 50 ml of methylene chloride, and 3.2 g of N,N-dimethylcarbamoyl chloride was added to the solution. The mixture was heated under refluxing and cooled, followed by washing with water. The organic layer was collected, and the solvent was distilled off. The residue was solidified by the addition of a mixed solvent of hexane and benzene. The solid obtained was collected by filtration and dried to obtain 2.0 g of N,N-dimethyl N'-(5-t-butyl-3-pyrazolyl)urea. This compound was recrystallized from hydrous methanol and found to have a melting point of 220° C. to 222° C.

EXAMPLE 11

Preparation of N,N-Dimethyl N'-(5-t-Butyl-4-chloro-3-pyrazolyl)urea (Compound No. 14)

2.1 g of Compound No. 13 as prepared in Example 10 was suspended in 30 ml of carbon tetrachloride, and 1.4 g of sulfuryl chloride was added dropwise to the suspension at 10° C. to 15° C. Further, the mixture was allowed to react at the same temperature for 2 hours, and a potassium carbonate aqueous solution was added to the reaction solution to form crystals. The crystals were collected by filtration and washed with water to obtain 1.4 g of N,N-dimethyl N'-(5-t-butyl-4-chloro-3-pyrazolyl)urea. The mass analysis of this compound showed molecular peaks at 244 and 246.

EXAMPLE 12

Preparation of N,N-Dimethyl N'-(5-t-Butyl-4-bromo-3-pyrazolyl)urea (Compound No. 15)

10 g of Compound No. 13 as prepared in Example 10 was dissolved in 50 ml of acetic acid, and 7.6 g of bromine was added dropwise to the solution. The mixture was allowed to react at room temperature for 3 hours, and the reaction solution was poured into ice water to form crystals. The crystals were collected by filtration and washed with water to obtain 11.7 g of N,N-dimethyl N'-(5-t-butyl-4-bromo-3-pyrazolyl)urea. The mass analysis of this compound showed molecular peaks at 288 and 300.

EXAMPLE 13

Preparation of N,N-Diethyl N'-(5-t-Butyl-3-pyrazolyl)urea (Compound No. 16)

4.2 g of Compound [II] was dissolved in 50 ml of methylene chloride, and 4.1 g of N,N-diethylcarbamoyl chloride was added to the solution. The mixture was heated under refluxing for 5 hours and cooled, followed by washing with water. The organic layer was collected, and the solvent was distilled off. The residue was subjected to crystallization by the addition of hexane. The crystals obtained were collected by filtration and dried to obtain 3.2 g of N,N-diethyl N'-(5-t-butyl-3-pyrazolyl)urea.

EXAMPLE 14

Preparation of Methyl N-(5-t-Butyl-3-pyrazolyl)carbamate (Compound No. 1)

42 g of Compound [II] and 30 g of sodium bicarbonate were dissolved in 2 l of water, and 34 g of methyl chloroformate was added dropwise to the solution over 1.5 hours at 10° C. The mixture was allowed to react at 10° C. for one hour. After completion of the reaction, the solid product was collected by filtration, washed with water and dried to obtain 44 g of methyl N-(5-t-butyl-3-pyrazolyl)carbamate.

The active compound according to this invention can be formulated into various formulations, e.g., emulsifiable concentrates, wettable powders, flowable formulations, dusts, granules, etc., by the application of a conventional manner for formulation.

Further, the compound of this invention can be mixed with other herbicides. Still further, in order to expand the scope of activity, the compound of this invention can be mixed with other pesticides than herbicides, such as plant growth regulators, insecticides, nematocides, fungicides, etc.

Typical formulations are explained by reference to the following Formulation Examples. In the Formulation Examples, all parts are by weight.

FORMULATION EXAMPLE 1

Preparation of Wettable Powder 50 parts of, as an active ingredient, each compound as shown in Table 1, 10 parts of diatomaceous earth, 35 parts of clay, 3 parts of sodium polyoxyethylene alkylaryl ether sulfonate and 2 parts of sodium alkylnaphthalenesulfonate were mixed and pulverized to obtain a wettable powder having 50% of the active ingredient.

In the use thereof, the wettable powder is diluted with water to a predetermined concentration and then subjected to spraying.

FORMULATION EXAMPLE 2

Preparation of Granule 5 parts of, as an active ingredient, each compound as shown in Table 1, 20 parts of bentonite, 73 parts of clay and 2 parts of sodium dodecylbenzenesulfonate were subjected to intimate mixing, and about 20 parts of water was added thereto. The resulting mixture was kneaded by means of a kneader, and passed through a granulator to form granules. The thus formed granules were dried and controlled in particle size to obtain granules having 5% of the active ingredient.

FORMULATION EXAMPLE 3

Preparation of Emulsifiable Concentrate 15 parts of, as an active ingredient, each compound as shown in Table 1, 40 parts of xylene, 40 parts of N,N-dimethylacetamide and 5 parts of polyoxyethylene alkylaryl ether were mixed to form a homogeneous solution. Thus, an emulsifiable concentrate having 15% of the active ingredient was obtained.

In the use thereof, the emulsifiable concentrate is diluted with water to a predetermined concentration and then subjected to spraying.

The pyrazole derivative represented by the formula [I] has excellent herbicidal activity. Therefore, it is effective for controlling weeds growing in upland farms, orchards, non-cultivated fields, etc. When this active compound is applied on the surface of a soil or mixed with a soil, it can inhibit the growth of weeds and ultimately result in withering thereof. Further, it can control growing weeds by foliar application.

If the amount of the compound of this invention applied is chosen within a range of from 0.5 to 10 kg/ha, it can be used as a selective herbicide in cultivation fields for corn, wheat, barley, sugar beet, soybeans, peanuts, sunflower, potato, cotton and fruits. Further, if the application amount is increased, the compound of this invention can be applied as a non-selective herbicide.

The compounds of this invention can, for example, be used for controlling dicotyledons, e.g., velvetleaf (*Abtilon theophrasti*), pigweed (*Amranthus retroflexus*), ragweed (*Ambrosia artemisiifolia*), aster (*Aster sublatus*), beggarticks (*Bidens pilosa*), moonflower. (*Calonyction muricatum*), shepherdspurse (*Capsella bursa-pastoris*), sicklepod (*Cassis obtusifolia*), lambsquarters (*Chenopodium album*), field bindweed (*Convolvulus arvensis*), jimsonweed (*Datura stramonium*), bedstraw (*Galium aparine*), morningglory (*Ipomea purpurea*), hembit (*Lamium amplexicaule*), pepperwood (*Lepidium virginicum*), woodsorrel (*Oxalis corniculata*), smartweed (*Polygonum spp.*), purslane (*Portulaca oleracea*), buttercup (*Rananculus repens*), fieldcress (*Rorippa indica*), pearlwort (*Sangina japonica*), groundsel (*Senecio vulgaris*), coffeebean (*Sesbania exaltata*), pricky sida (*Sida spinosa*), nightshade (*Solanum nigrum*), spiny sowthistle (*Sunchus asper*), chickweed (*Sterallia midia*), vetch (*vicia sativa*), cocklebur (*Xanthium pensylvanicum*), etc.; monocotyledons, e.g., quackgrass (*Agropyron repens*), meadow foxtail (*Alopeculus pratensis*), wild oat (*Avena fatus*), crabgrass (*Digitaria sanguinalis*), barnyardgrass (*Echinochloa crus-galli*), goosegrass (*Eleusine indica*), Italian ryegrass (*lorium multiflorum*), fall panicum (*Panicum dichotomiflorum), bluegrass (Poa anua), buckwheat (Polygonum convulvulus), giant foxtail (Setaria faberii), green foxtail (Setaria viridis), Johnsongrass (Sorghum halepens), etc.; and perennial weeds, e.g., flatsedge (Cyperus iria), kyllinga (Kyllinga brevifolia), etc.

As described above, the compound of this invention has an excellent herbicidal activity against a wide range of weeds. The present invention can exhibit markedly high herbicidal activity when applied to the surface of a soil or to the foliar portions of weeds just before or after the germination of the weeds.

Further, when the compound of this invention is mixed with soil, it can also exhibit quite high herbicidal activity.

In order to explain the herbicidal activity of the compounds of the present invention, a series of Test Examples are shown.

TEST EXAMPLE 1

Pre-Emergence Soil Treatment

Pots of 100 cm$^2$ were packed with volcanic ash soil and predetermined amounts of seeds of crabgrass (Digitaria sanguinalis), edible barnyardgrass (Echinochloa crus-galli), smartweed (Polygonum nodosum), pigweed (Amaranthus retroflexus), corn (Zea mays), wheat (Triticum aestivum) and mung beans (Phaseolus radiatus) were sown in each pot, followed by covering with soil to a depth of about 5 mm. On the same day, a wettable powder containing each compound as shown in Table 2 was diluted with water and applied to the surface of the soil in each pot in an amount of active ingredient of 10 kg/ha. The herbicidal activity was visually evaluated two weeks after the application. The results obtained are shown in Table 2. Ratings of growth inhibition shown in Table 2 were given on a scale of 0–5 grades in which the grade 5 indicates a complete kill of the plant and the grade 0 no inhibition or substantially no inhibition.

5 = complete kill
4 = 80–99% damage
3 = 60–79% damage
2 = 40–59% damage
1 = 20–39% damage
0 = 0–19% damage

TABLE 2

| Compound No. | Herbicidal Activity | | | | | | |
|---|---|---|---|---|---|---|---|
| | A | B | C | D | E | F | G |
| 1 | 5 | 5 | 5 | 5 | 3 | 5 | 5 |
| 2 | 5 | 5 | 5 | 5 | 1 | 4 | 5 |
| 3 | 3 | 2 | 5 | 5 | 0 | 0 | 5 |
| 4 | 3 | 1 | 5 | 5 | 0 | 0 | 0 |
| 5 | 2 | 0 | 4 | 3 | 0 | 0 | 0 |
| 6 | 5 | 4 | 5 | 5 | 1 | 2 | 5 |
| 7 | 5 | 5 | 5 | 5 | 4 | 5 | 5 |
| 8 | 5 | 5 | 4 | 5 | 5 | 5 | 2 |
| 10 | 5 | 5 | 5 | 5 | 4 | 5 | 5 |
| 11 | 5 | 5 | 5 | 5 | 1 | 5 | 5 |
| 12 | 5 | 5 | 5 | 5 | 2 | 2 | 4 |
| 13 | 5 | 4 | 5 | 5 | 3 | 5 | 5 |
| 14 | 4 | 3 | 5 | 5 | 0 | 2 | 2 |
| 15 | 2 | 2 | 3 | 4 | 0 | 0 | 0 |

A: Crabgrass (Digitaria sanguinalis)
B: Edible Barnyardgrass (Echinochloa crus-galli)
C: Smartweed (Polygonum nodosum)
D: Pigweed (Amaranthus retroflexus)
E: Corn (Zea mays)
F: Wheat (Triticum aestivum)
G: Mung beans (Phaseolus radiatus)

TEST EXAMPLE 2

Foliar Spray (Post-Emergence) Treatment

Ceramic pots of 100 cm$^2$ were packed with volcanic ash soil and predetermined amounts of seeds of crabgrass (Digitaria sanguinalis), edible barnyardgrass (Echinochloa crus-galli), smartweed (Polygonum nodosum), pigweed (Amaranthus retroflexus), corn (Zea mays), wheat (Triticum aestivum) and mung beans (Phaseolus radiatus) were sown, followed by covering with soil to a depth of about 1 cm. The resulting pots were allowed to stand in a green house. When the respective plants grew up to a 1–2 leaf stage, a wettable powder containing each compound as shown in Table 3 was diluted with 1000 l/ha of water and applied foliarly to the plants by means of a sprayer in an amount of active ingredient of 10 kg/ha. Ten days after the application, the herbicidal activity was visually evaluated on the same scale as in Test Example 1. The results obtained are shown in Table 3.

TABLE 3

| Compound No. | Herbicidal Activity | | | | | | |
|---|---|---|---|---|---|---|---|
| | A | B | C | D | E | F | G |
| 1 | 5 | 5 | 5 | 5 | 3 | 5 | 5 |
| 2 | 5 | 5 | 5 | 5 | 1 | 4 | 5 |
| 3 | 3 | 2 | 5 | 5 | 0 | 0 | 5 |
| 4 | 3 | 1 | 5 | 5 | 0 | 0 | 0 |
| 5 | 2 | 0 | 4 | 3 | 0 | 0 | 0 |
| 6 | 5 | 4 | 5 | 5 | 1 | 2 | 5 |
| 7 | 5 | 5 | 5 | 5 | 4 | 5 | 5 |
| 8 | 2 | 3 | 3 | 2 | 3 | 4 | 5 |
| 9 | 5 | 2 | 5 | 5 | 2 | 2 | 5 |
| 10 | 5 | 5 | 5 | 5 | 5 | 5 | 5 |
| 11 | 5 | 5 | 5 | 5 | 5 | 5 | 5 |
| 12 | 5 | 5 | 5 | 5 | 4 | 5 | 5 |
| 13 | 5 | 5 | 5 | 5 | 4 | 3 | 5 |
| 14 | 4 | 3 | 5 | 5 | 3 | 2 | 5 |
| 15 | 2 | 2 | 4 | 4 | 5 | 2 | 5 |
| 16 | 4 | 4 | 5 | 5 | 5 | 5 | 5 |

A: Crabgrass (Digitaria sanguinalis)
B: Edible Barnyardgrass (Echinochloa crus-galli)
C: Smartweed (Polygonum nodosum)
D: Pigweed (Amaranthus retroflexus)
E: Corn (Zea mays)
F: Wheat (Triticum aestivum)
G: Mung beans (Phaseolus radiatus)

TEST EXAMPLE 3

Pre-Emergence Soil Treatment

Pots of 325 cm$^2$ were packed with loam soil and predetermined amounts of seeds of crabgrass (Digitaria sanguinalis), green foxtail (Setaria viridis), smartweed (Polygonum nodosum), pigweed (Amaranthus retroflexus), lambsquarters (Chenopodium album), pricky sida (Sida spinosa), corn, sorghum, wheat, peanuts, soybeans, cotton and sunflower were sown in each pot, followed by covering with soil to a depth of about 2 cm. On the same day, a wettable powder containing each of Compound Nos. 1 and 13 was diluted with water and applied to the surface of the soil in each pot in an amount of active ingredient of 2 kg/ha and 4 kg/ha, respectively. The herbicidal activity was visually evaluated two weeks after the application. The results obtained are shown in Table 4. Ratings of growth inhibition shown in Table 4 were given on a scale of 0–5 grades in which the grade 5 indicates a complete kill of the plant and the grade 0 no inhibition or substantially no inhibition.

5 = complete kill
4 = 80–90% damage

3 = 60-79% damage
2 = 40-59% damage
1 = 20-39% damage
0 = 0-19% damage

TABLE 4

| Compound No. | Amount of A.I. (kg/ha) | Herbicidal Activity |  |  |  |  |  |  |  |  |  |  |  |  |
|---|---|---|---|---|---|---|---|---|---|---|---|---|---|---|---|
| | | A | B | C | D | E | F | G | H | I | J | K | L | M |
| 1 | 2 | 5 | 4 | 5 | 5 | 5 | 5 | 0 | 0 | 3 | 0 | 3 | 3 | 2 |
| | 4 | 5 | 5 | 5 | 5 | 5 | 5 | 1 | 1 | 5 | 0 | 5 | 5 | 4 |
| 13 | 2 | 5 | 4 | 5 | 5 | 5 | 5 | 0 | 0 | 2 | 0 | 0 | 0 | 0 |
| | 4 | 5 | 5 | 5 | 5 | 5 | 5 | 0 | 2 | 2 | 0 | 0 | 2 | 1 |

A: Crabgrass (*Digitaria sanguinalis*)
B: Green Foxtail (*Setaria viridis*)
C: Smartweed (*Polygonum nodosum*)
D: Pigweed (*Amaranthus retroflexus*)
E: Lambsquarters (*Chenopodium album*)
F: Pricky Sida (*Sida spinosa*)
G: Corn
H: Sorghum
I: Wheat
J: Peanuts
K: Soybeans
L: Cotton
M: Sunflower

TEST EXAMPLE 4

Pre-Emergence Treatment in Paddy Condition

Ceramic pots of 120 cm² were packed with paddy soil and predetermined amounts of seeds of barnyardgrass (*Echinochloa crus-galli*) and pickerelweed (*Monochoria vaginalis*) were incorporated in soil to a depth of about 2 cm from the surface layer. Two plants of slender spikerush (*Eleocharis acicularis*) and two rice plants having a 2-leaf stage were transplanted respectively in each pot, and the depth of water was maintained at about 3 cm. Three days later, a wettable powder containing each compound as shown in Table 5 prepared in the same manner as in Formulation 1 was administered to water in an amount of active ingredient of 10 kg/ha. Three weeks after the treatment, the ratings of growth of the plants were visually evaluated on the same scale as in Test Example 1. The results obtained are shown in Table 5.

TABLE 5

| Compound No. | Herbicidal Activity |  |  |  |
|---|---|---|---|---|
| | A | B | C | D |
| 1 | 5 | 5 | 4.5 | 5 |
| 2 | 5 | 5 | 4 | 5 |
| 3 | 3 | 4 | 1 | 2 |
| 4 | 3 | 4 | 2 | 3 |
| 5 | 2 | 3 | 0 | 0 |
| 6 | 5 | 5 | 4.5 | 5 |
| 7 | 5 | 5 | 4 | 5 |
| 8 | 5 | 4.5 | 4.5 | 4.5 |
| 9 | 5 | 2 | 2 | 0 |
| 10 | 5 | 5 | 4 | 5 |
| 11 | 4 | 4 | 3 | 5 |
| 12 | 4 | 2 | 3 | 0 |
| 13 | 5 | 5 | 4 | 5 |
| 14 | 3 | 4 | 0 | 4.5 |
| 15 | 3 | 4 | 4 | 0 |
| 16 | 4 | 4 | 3 | 3 |

A: Barnyardgrass (*Echinochloa crus-galli*)
B: Pickerelweed (*Monochoria vaginalis*)
C: Slender Spikerush (*Eleocharis acicularis*)
D: Rice Plant As is clear from Table 5 above, the compounds according to this invention are effective for controlling the weeds that are serious weeds in the paddy field. The compounds of this invention, however, had adverse effects on rice plants.

While the invention has been described in detail and with reference to specific embodiments thereof, it will be apparent to one skilled in the art that various changes and modifications can be made therein without departing from the spirit and scope thereof.

What is claimed is:

1. A pyrazole derivative represented by the formula [I]:

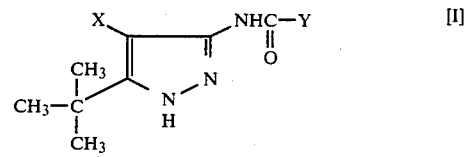

wherein X is a hydrogen atom, a chlorine atom or a bromine atom; and Y is (1) an —OR group wherein R is a lower alkyl group, a lower alkenyl group, or a lower alkynyl group, or (2) an

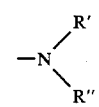

group wherein R' and R", which may be the same or different, are each a lower alkyl group.

2. A pyrazole derivative as claimed in claim 1, wherein Y is an —OR group wherein R is the same as defined in claim 1.

3. A pyrazole derivative as claimed in claim 1, wherein Y is an

group wherein R' and R" are the same as defined in claim 1.

4. Methyl N-(5-t-butyl-3-pyrazolyl)carbamate, as claimed in claim 1.

5. Allyl N-(5-t-butyl-3-pyrazolyl)carbamate, as claimed in claim 1.

6. Propargyl N-(5-t-butyl-3-pyrazolyl)carbamate, as claimed in claim 1.

7. N,N-Dimethyl-N'-(5-t-butyl-3-pyrazolyl)urea, as claimed in claim 1.

8. A herbicide composition against weeds comprising a herbicidally effective amount of a pyrazole derivative represented by the formula [I] as an active ingredient:

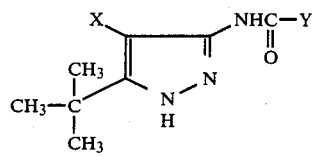
[I]

wherein X is a hydrogen atom, a chlorine atom or a bromine atom; and Y is (1) an —OR group wherein R is a lower alkyl group, a lower alkenyl group, or a lower alkynyl group, or (2) an

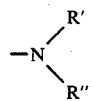

group wherein R' and R", which may be the same or different, are each a lower alkyl group and a carrier.

9. A method for inhibiting the growth of weeds comprising applying to a plant or locus, a herbicidally effective amount of a pyrazole derivative represented by the formula [I]:

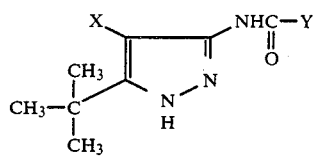
[I]

wherein X is a hydrogen atom, a chlorine atom or a bromine atom; and Y is (1) an —OR group wherein R is a lower alkyl group, a lower alkenyl group, or a lower alkynyl group, or (2) an

group wherein R' and R", which may be the same or different, are each a lower alkyl group.

* * * * *